(12) United States Patent  (10) Patent No.: US 10,265,467 B2
Mao  (45) Date of Patent: *Apr. 23, 2019

(54) NEEDLE DEVICE

(71) Applicant: GEMTIER MEDICAL (SHANGHAI) INC., Shanghai (CN)

(72) Inventor: Yaling Mao, Shanghai (CN)

(73) Assignee: GEMTIER MEDICAL (SHANGHAI) INC., Shanghai (CN)

( * ) Notice: Subject to any disclaimer, the term of this patent is extended or adjusted under 35 U.S.C. 154(b) by 205 days.

This patent is subject to a terminal disclaimer.

(21) Appl. No.: 15/353,041

(22) Filed: Nov. 16, 2016

(65) Prior Publication Data

US 2017/0143897 A1 May 25, 2017

(30) Foreign Application Priority Data

Nov. 23, 2015 (CN) .......................... 2015 1 0818147
Nov. 23, 2015 (CN) ...................... 2015 2 0939839 U

(51) Int. Cl.
*A61M 5/158* (2006.01)

(52) U.S. Cl.
CPC ..... *A61M 5/158* (2013.01); *A61M 2005/1585* (2013.01); *A61M 2005/1586* (2013.01); *A61M 2005/1587* (2013.01)

(58) Field of Classification Search
CPC .......... A61M 5/158; A61M 2005/1587; A61M 2005/1585; A61M 2005/1586; A61M 5/3243
See application file for complete search history.

(56) References Cited

U.S. PATENT DOCUMENTS 4,804,372 A 2/1989 Laico et al.
4,946,447 A 8/1990 Hardcastle et al.
(Continued)

FOREIGN PATENT DOCUMENTS

AU 2015336700 B2 1/2017
BR 102016027251 A2 5/2017
(Continued)

OTHER PUBLICATIONS

International Search Report issued in International Patent Application No. PCT/CN2016/105650 dated Dec. 29, 2016.
(Continued)

*Primary Examiner* — Amber R Stiles
(74) *Attorney, Agent, or Firm* — Harness, Dickey & Pierce, P.L.C.

(57) ABSTRACT

The present invention discloses a needle device, comprising a needle base and a needle head being placed in the needle base, a first sleeve part slides on the needle base, a second sleeve part slides on the first sleeve part; at least one protrusion portion is arranged on upper surface of the needle base, a through hole is arranged at a rear end of the first sleeve part, at least one elastic limit portion is arranged in the through hole, the elastic limit portion prevents the protrusion portion from moving toward fixed end of the elastic limit portion when the protrusion portion moves to position between inner wall of the through hole and free end of the elastic limit portion; a limit apparatus is also arranged between the first sleeve part and the second sleeve part. After use of the needle device of the present invention, the needle head can be covered quickly by the sleeve part on the needle base, and the connection between the sleeve part and needle base is tight, the sleeve part will not rebound, security of products is improved effectively.

20 Claims, 9 Drawing Sheets

(56) References Cited

U.S. PATENT DOCUMENTS

| | | | |
|---|---|---|---|
| 5,562,631 | A | 10/1996 | Bogert |
| 5,573,512 | A | 11/1996 | van den Haak |
| 10,022,505 | B2 | 7/2018 | Hu |
| 2003/0073956 | A1 | 4/2003 | Hoffman et al. |
| 2003/0163095 | A1 | 8/2003 | Nakashima |
| 2005/0137528 | A1 | 6/2005 | Wilkinson |
| 2012/0179119 | A1 | 7/2012 | Ng et al. |
| 2013/0245564 | A1* | 9/2013 | Cheng .............. A61M 5/3202 604/195 |

FOREIGN PATENT DOCUMENTS

| | | |
|---|---|---|
| CN | 201840729 U | 5/2011 |
| CN | 202478304 U | 10/2012 |
| CN | 202590082 U | 12/2012 |
| CN | 103357090 A | 10/2013 |
| CN | 104288866 A | 1/2015 |
| CN | 204181959 U | 3/2015 |
| CN | 104491955 A | 4/2015 |
| CN | 204395141 U | 6/2015 |
| CN | 204410825 U | 6/2015 |
| CN | 204411410 U | 6/2015 |
| CN | 204411424 U | 6/2015 |
| CN | 104288866 B | 7/2015 |
| CN | 205649700 U | 10/2016 |
| CN | 106730139 A | 5/2017 |
| EP | 1362612 A1 | 11/2003 |
| EP | 3093034 A1 | 11/2016 |
| JP | H07328119 A | 12/1995 |
| JP | H09099070 A | 4/1997 |
| JP | 2002000727 A | 1/2002 |
| JP | 4654102 B2 | 3/2011 |
| JP | 201718045 A | 1/2017 |
| JP | 2017094072 A | 6/2017 |
| TW | 200735907 A | 10/2007 |
| WO | WO-2017088675 A1 | 6/2017 |

OTHER PUBLICATIONS

Written Opinion of the International Searching Authority issued in International Patent Application No. PCT/CN2016/105650 dated Dec. 29, 2016.
International Search Report issued in International Patent Application No. PCT/CN2016/106819 dated Feb. 16, 2017.
Written Opinion of the International Searching Authority issued in International Patent Application No. PCT/CN2016/106819 dated Feb. 16, 2017.
Notification of Reasons for Refusal of JP2017094072A(PCT/CN2016/105650) dated Sep. 7, 2017.
Search Report by Registered Searching Organization of JP2017094072A(PCT/CN2016/105650) dated Sep. 4, 2017.
1st Office Action issued in TW201718045A.
The First Office Action and Search Report of Priority Application CN201510818147.6 dated Aug. 2, 2018.
The Extended European Search Report issued in European Patent Application No. 16867960.3 dated Jun. 15, 2018.
Notification of Reasons for Refusal issued in Japanese Patent Application No. 2017553239 dated Aug. 7, 2018.
The First Examination Report issued in Australian Patent Application No. 2016359516 dated Apr. 20, 2018.
Examination Report issued in Pakistan Patent Application No. 7212016 dated Jun. 29, 2018.

* cited by examiner

NEEDLE DEVICE

CROSS REFERENCE

The present application claims priority of Chinese Patent Application 201510818147.6 and 201520939839.1, filed Nov. 23, 2015, the contents of which are incorporated herein by reference in their entireties.

FIELD OF INVENTION

The present invention relates to a needle device.

PRIOR ARTS

The needle devices such as intravenous needles in prior arts are usually used once. It is necessary to discard the needle device after use as a medical waste. A needle sleeve is usually added on the needle base to avoid the needle head injuring human or objects when discarding the needle device. However, the needle devices in prior arts have the defects that the needle sleeve is easy to rebound, which causes exposure of the needle head.

CONTENT OF THE PRESENT INVENTION

The technical problem to be solved in the present invention is for overcoming the defects that the needle sleeve of the needle device in prior arts is easy to rebound, and a needle device is provided.

The present invention solves the above-mentioned technical problems through the following technical solutions:

A needle device, comprising a needle base and a needle head being placed in the needle base, wherein a first sleeve part slides on the needle base, a second sleeve part slides on the first sleeve part; at least one protrusion portion is arranged on upper surface of the needle base, a through hole is arranged at a rear end of the first sleeve part, at least one elastic limit portion is arranged in the through hole, the elastic limit portion prevents the protrusion portion from moving toward fixed end of the elastic limit portion when the protrusion portion moves to a position between inner wall of the through hole and free end of the elastic limit portion; a limit apparatus is also arranged between the first sleeve part and the second sleeve part.

Preferably, the limit apparatus comprises a first blocking portion, a second blocking portion, a third blocking portion and an elastic button; the first blocking portion and the second blocking portion are arranged on upper surface of the first sleeve part, the elastic button is arranged on upper surface of the second sleeve part, the third blocking portion is arranged on lower surface of the second sleeve part, the second blocking portion prevents the third blocking portion from further moving when the elastic button moves to a position in front of the first blocking portion. Such that the first sleeve part is hard to rebound.

Preferably, the first sleeve part further has a bar groove, the bar groove is communicated with the through hole, the bar groove is located above the protrusion portion. The bar groove can be a passageway of the protrusion portion, and in addition, the configuration of the protrusion portion can decrease the weight of the first sleeve part.

Preferably, the needle device comprises two elastic limit portions, two elastic limit portions are separately located at both sides of the bar groove. Two elastic limit portions can further improves the restriction on the protrusion portion, preventing the first sleeve part rebounding effectively.

Preferably, the distance between the free ends of two elastic limit portions is less than the distance between the fixed ends of two elastic limit portions. Such that the restriction on the protrusion portion is improved effectively, preventing the first sleeve part rebounding effectively.

Preferably, the needle device comprises two elastic limit portions, two elastic limit portions are both located at one side of the bar groove; the needle device comprises two protrusion portions, two protrusion portions match with two elastic limit portions respectively. Such that the restriction on the protrusion portion is further improved, preventing the first sleeve part rebounding effectively.

Preferably, the needle device comprises four elastic limit portions, two elastic limit portions are located at one side of the bar groove, and the other two elastic limit portions are located at the other side of the bar groove. Such that the restriction on the protrusion portion is further improved, preventing the first sleeve part rebounding effectively.

Preferably, the first blocking portion comprises two strip portions, the strip portions are arranged on upper surface of the first sleeve part, two strip portions are arranged to be parallel to each other, and the strip portions act as a sliding track of the third blocking portion. Such that the third blocking portion can slide successfully, and it is also realized to block the elastic button, thereby preventing the second sleeve part rebounding.

Preferably, a cushion is arranged at bottom of the second sleeve part, bottom of the cushion is a flat surface, and the needle base and the first sleeve part are arranged inside the space surrounded by the cushion and the second sleeve part. The cushion directly contacts with skin of human body when using, such that the cushion with the flat surface can fits with skin of human body tight, thereby improving comfort level of the skin during using the device.

Preferably, a clamping portion is arranged at lower section of the second sleeve part, and the cushion is clamped by the clamping portion. So as to facilitate the connection of the cushion and the second sleeve part.

Preferably, the cushion and the second sleeve part are integrally formed. So as to have advantage that it is convenient to manufacture, the cushion needs not to be installed additionally.

Preferably, the needle head is arranged on front end of the needle base, vertical distance between the needle head and the bottom of the cushion is larger than 0.05 mm. Such that the needle head is close to skin of human body when using, thereby improving comfort level when using the device.

Preferably, length of the needle base is larger than 2 mm, length of the first sleeve part is larger than 2 mm, and length of the second sleeve part is larger than 2 mm. Such that the needle head can be covered effectively after the first sleeve part is pulled away from the second sleeve part, thereby improving security of the device.

Preferably, each of both sides of the needle base has a first slide railway, the first sleeve part has a first slide track matching with the first slide railway; each of both sides of the first sleeve part has a second slide railway, the second sleeve part has a second slide track matching with the second slide railway. Such that the needle base, the first sleeve part and the second sleeve part can connected tight, and slide smoothly.

Preferably, a pressing portion is arranged on upper surface of the second sleeve part. Such that after use of the needle device, the operator can press the pressing portion on the second sleeve part, extract the needle head from skin of human body easily.

Preferably, an operating handle is arranged at rear end of the needle base, the operating handle is provided with at least one wing portion. The operation handle makes the operation of the needle device more convenient.

Preferably, the needle device comprises one wing portion, the wing portion is located at one side of the needle base. The operator can grabs the wing portion to realize the operation of the needle device.

Preferably, the needle device comprises two wing portions, the wing portions are located at both sides of the needle base separately. Two wing portions make the operation of the needle device more convenient.

Preferably, the operating handle is sleeved with the needle base, or the operating handle is integrally formed with the needle base, or the operating handle is clamped by the needle base.

Preferably, the operating handle further comprises a bent portion, the bent portion is arranged between the wing portion and the needle base. The operating handle which can be bent has advantage of easy operating.

Preferably, both of the first sleeve part and the second sleeve part are slot shaped. The slot shaped sleeve part is easy to operate.

The positive effect of the present invention lies in: the needle device of the present invention has advantages that the operator operates conveniently when using, and the skin of patients is comfortable, the needle head can be covered quickly by the sleeve part on the needle base after use, and the connection between the sleeve part and needle base is tight, the sleeve part will not rebound, security of products is improved effectively.

DETAILED DESCRIPTION OF THE PREFERRED EMBODIMENT

Figure 1:
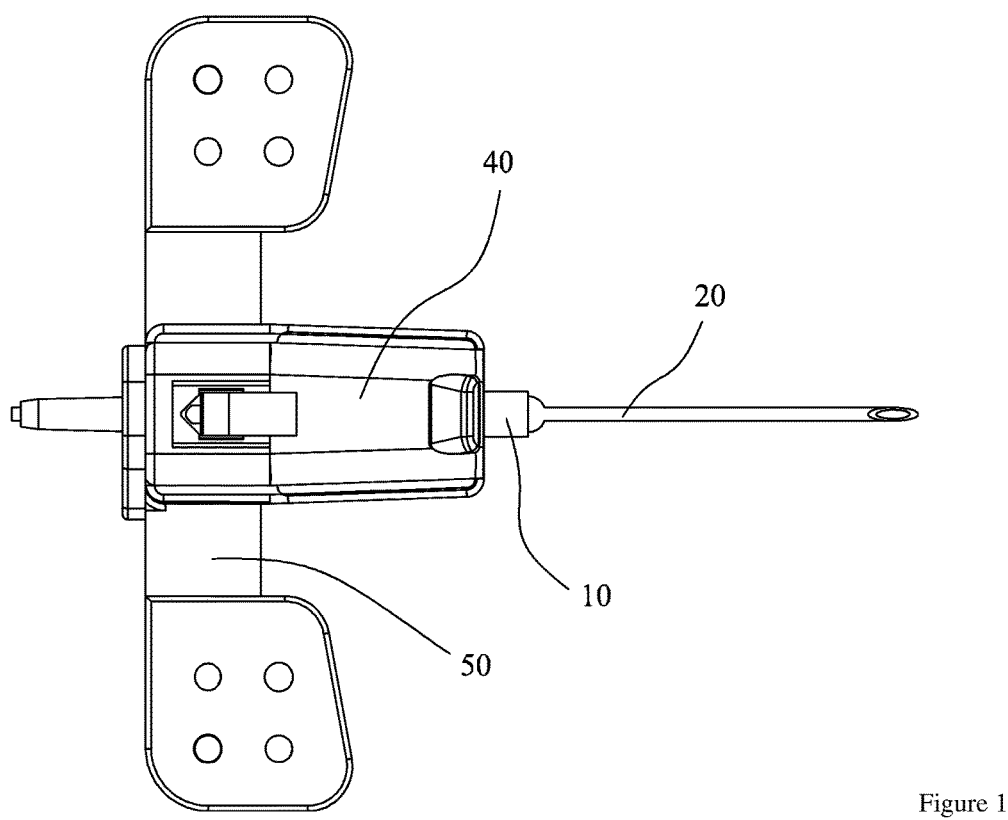
FIG. 1 is a schematic structure view of a preferred embodiment of the present invention.
Figure 2:
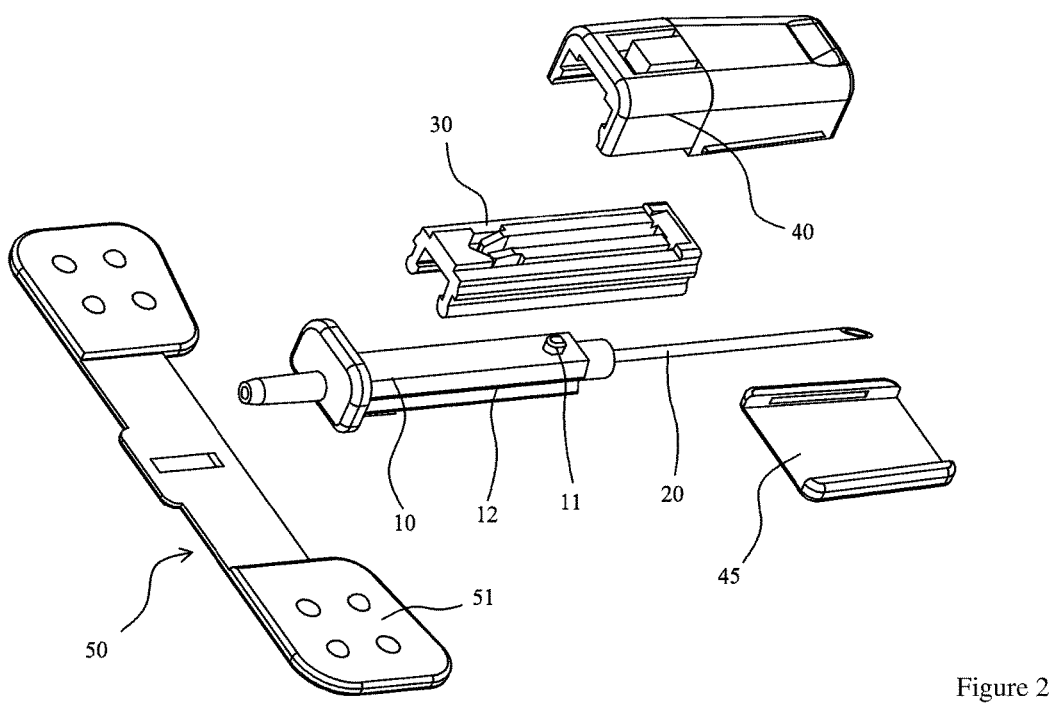
FIG. 2 is a three-dimensional assembly view of a preferred embodiment of the present invention.
Figure 3:
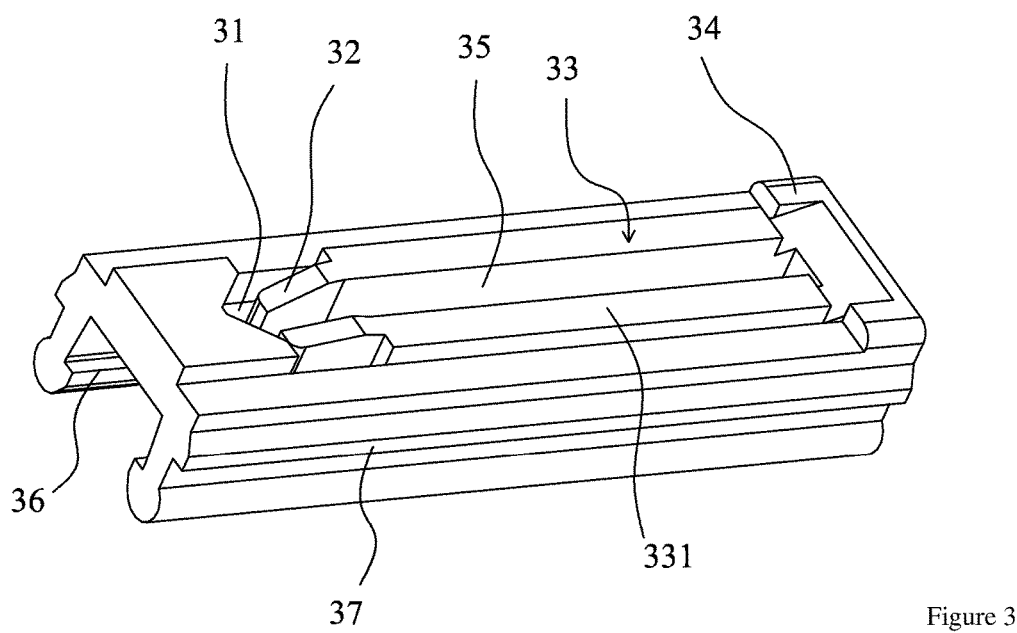
FIG. 3 is a schematic three-dimensional view of the first sleeve part in a preferred embodiment of the present invention.
Figure 4:
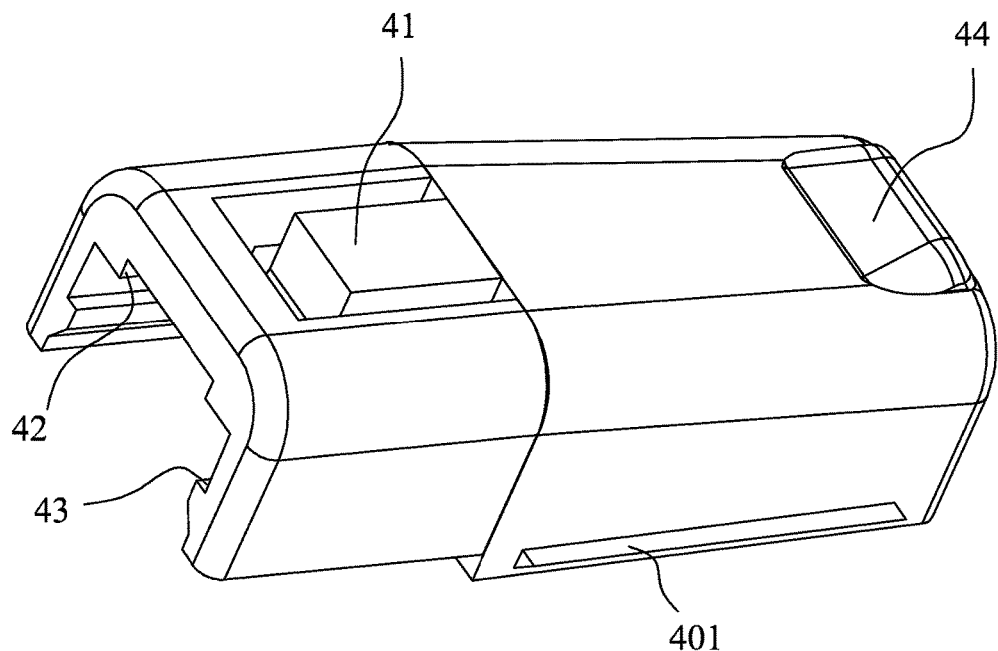
FIG. 4 is a schematic three-dimensional view of the second sleeve part in a preferred embodiment of the present invention.
Figure 5:
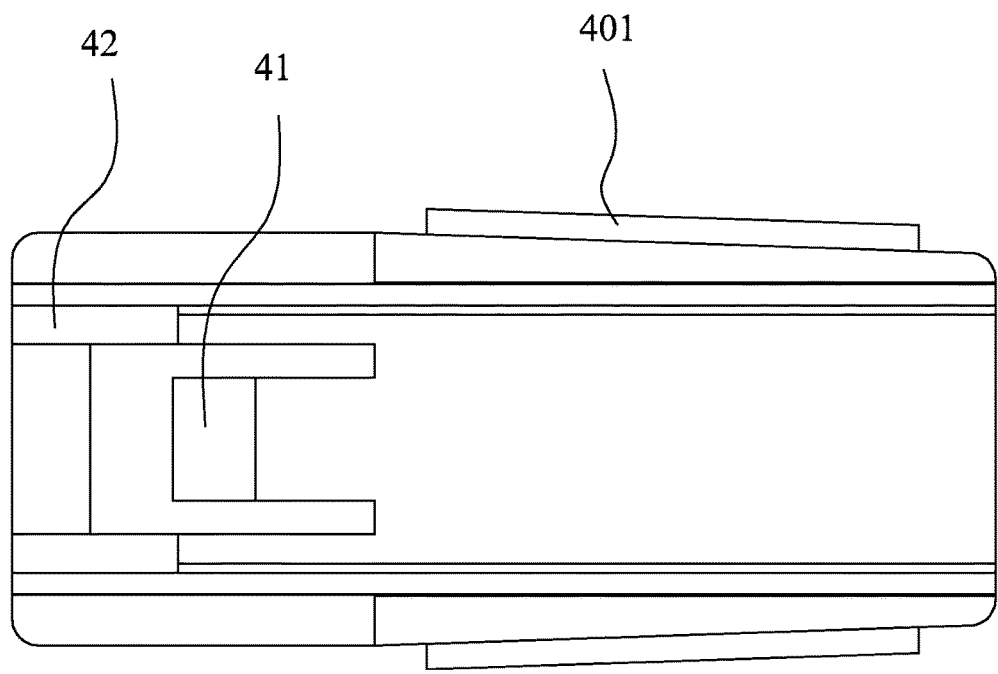
FIG. 5 is a schematic bottom view of the second sleeve part in a preferred embodiment of the present invention.

Below presents preferred embodiments based on the drawings in order to illustrate the present invention more clearly and completely.

As shown in FIG. 1, FIG. 2, FIG. 3, FIG. 4, FIG. 5, FIG. 6, FIG. 7, FIG. 8, FIG. 9, and FIG. 10, a needle device, comprising a needle base 10 and a needle head 20 connecting to a front end of the needle base 10, a first sleeve part 30 slides on the needle base 10, a second sleeve part 40 slides on the first sleeve part 30; a protrusion portion 11 is arranged on upper surface of the needle base 10, a through hole 31 is arranged at a rear end of the first sleeve part 30, an elastic limit portion 32 is arranged in the through hole 31, the elastic limit portion 32 prevents the protrusion portion 11 from move toward fixed end of the elastic limit portion 32 when the protrusion portion 11 moves to a position between inner wall of the through hole 31 and free end of the elastic limit portion 32; a limit apparatus is also arranged between the first sleeve part 30 and the second sleeve part 40, the limit apparatus comprises a first blocking portion 33, a second blocking portion 34, a third blocking portion 42 and an elastic button 41; the first blocking portion 33 and the second blocking portion 34 are arranged on upper surface of the first sleeve part 30, the elastic button 41 is arranged on upper surface of the second sleeve part 40, the third blocking portion 42 is arranged on lower surface of the second sleeve part 40, the second blocking portion 34 prevents the third blocking portion 42 from further moving when the elastic button 41 moves to a position front of the first blocking portion 33.

The first sleeve part 30 further has a bar groove 35, the bar groove 35 is communicated with the through hole 31, the bar groove 35 is located above the protrusion portion 11. The needle device comprises two elastic limit portions 32, two elastic limit portions 32 are separately located at both sides of the bar groove 35. The distance between the free ends of two elastic limit portions 32 is less than the distance between the fixed ends of two elastic limit portions 32.

There may be two elastic limit portions and two protrusion portions, two elastic limit portions are both located at one side of the bar groove, two protrusion portions match with two elastic limit portions respectively. In this way the restriction on the protrusion portion can be improved, to prevent the first sleeve part rebounding.

There may be four elastic limit portions, two elastic limit portions are located at one side of the bar groove, and the other two elastic limit portions are located at the other side of the bar groove. The increase of the elastic limit portions further improves the restriction on the protrusion portion.

The first blocking portion 33 comprises two strip portions 331, the strip portions 331 are arranged on upper surface of the first sleeve part 30, two strip portions 331 are arranged to be parallel to each other, and the strip portions 331 act as a sliding track of the third blocking portion 42.

A cushion 45 is arranged at bottom of the second sleeve part 40, bottom of the cushion is a flat surface, and the needle base 10 and the first sleeve part 30 are arranged inside the space surrounded by the cushion 45 and the second sleeve part 40. The cushion 45 and the second sleeve part 40 may be manufactured separately and then be assembled, at this moment, a clamping portion 401 may be arranged at lower section of the second sleeve part 40, and the cushion 45 is clamped by the clamping portion 401. In addition, the cushion 45 and the second sleeve part 40 can also be integrally formed. Both of the first sleeve part 30 and the second sleeve part 40 are slot shaped.

Vertical distance between the needle head 20 and the bottom of the cushion 45 is larger than 0.05 mm. In this way distance between the needle head and skin of human body can be smaller, so as to improve comfort level of needle device when using. Length of the needle base 10 is larger than 2 mm, length of the first sleeve part 30 is larger than 2 mm, and length of the second sleeve part 40 is larger than 2 mm.

Each of both sides of the needle base 10 has a first slide railway 12, the first sleeve part 30 has a first slide track 36 matching with the first slide railway 12; each of both sides of the first sleeve part 30 has a second slide railway 37, the second sleeve part 40 has a second slide track 43 matching with the second slide railway 37.

A pressing portion 44 is arranged on upper surface of the second sleeve part 40. In this way, after use of the needle device, the user can press the pressing portion on the second sleeve part, to easily slide the second sleeve part.

Figure 6:
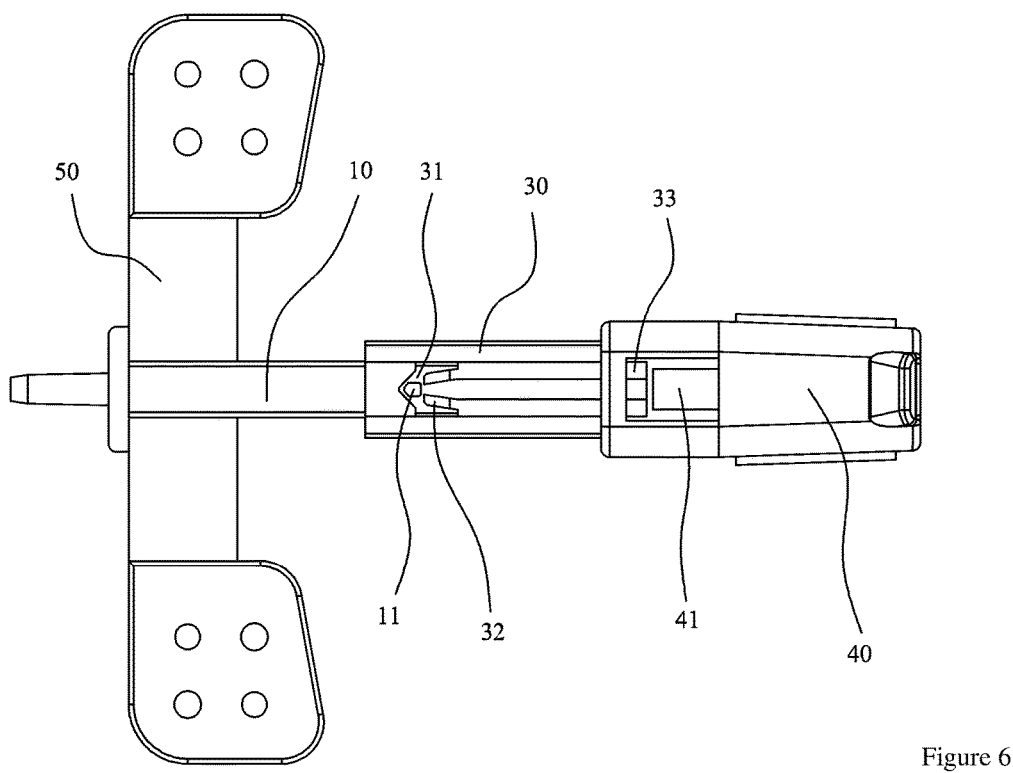
FIG. 6 is a schematic plan view of a preferred embodiment of the present invention after use.
Figure 7:
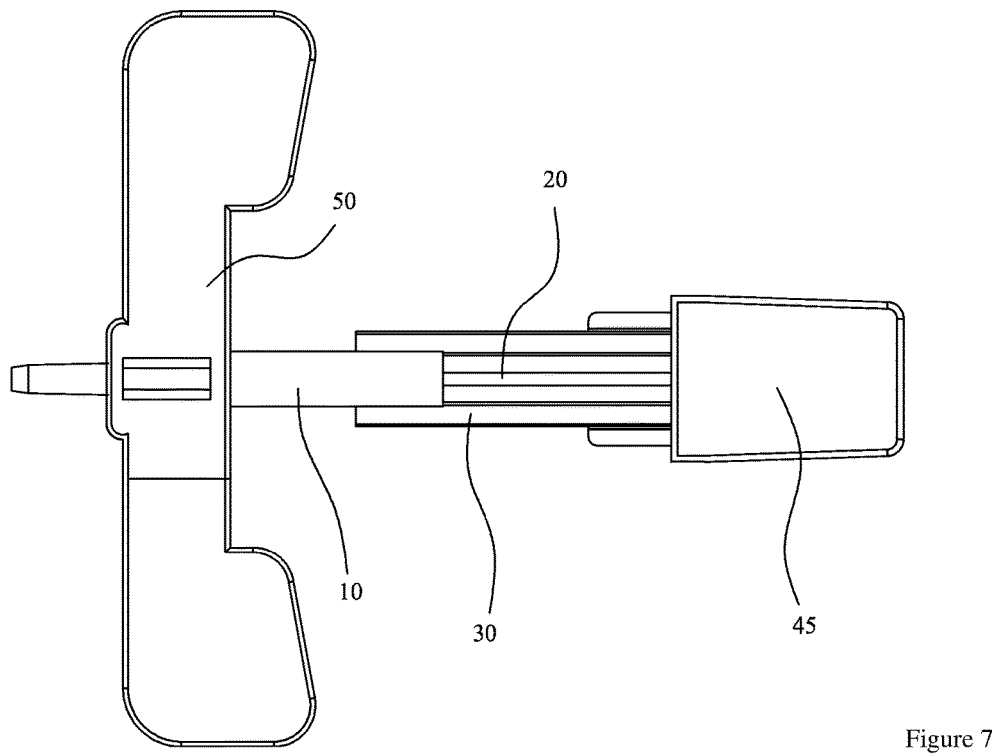
FIG. 7 is a schematic bottom view of a preferred embodiment of the present invention after use.
Figure 8:
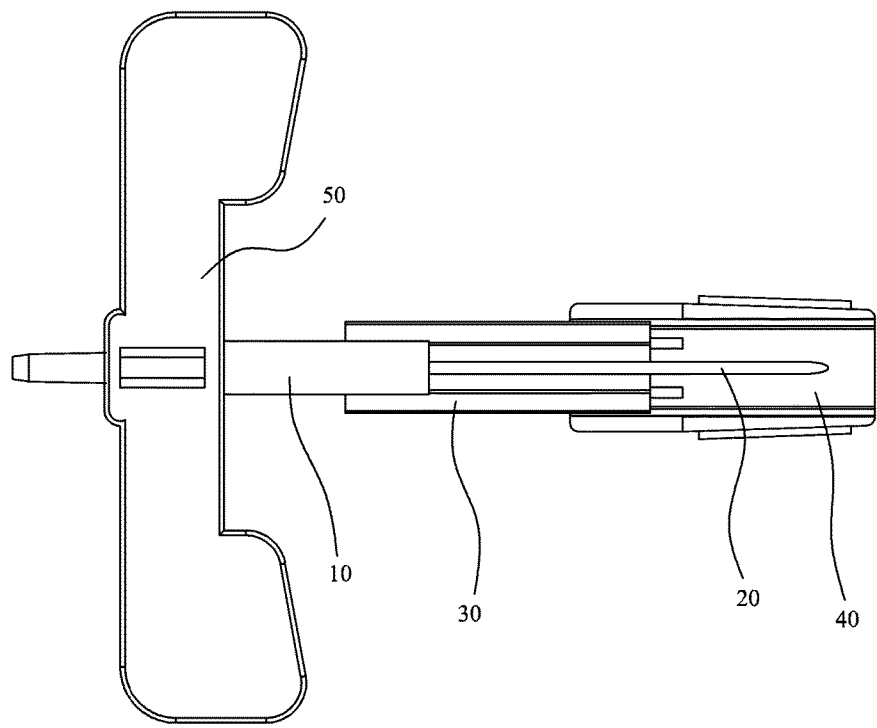
FIG. 8 is a schematic bottom view of a preferred embodiment of the present invention after use when a cushion is not installed.
Figure 9:
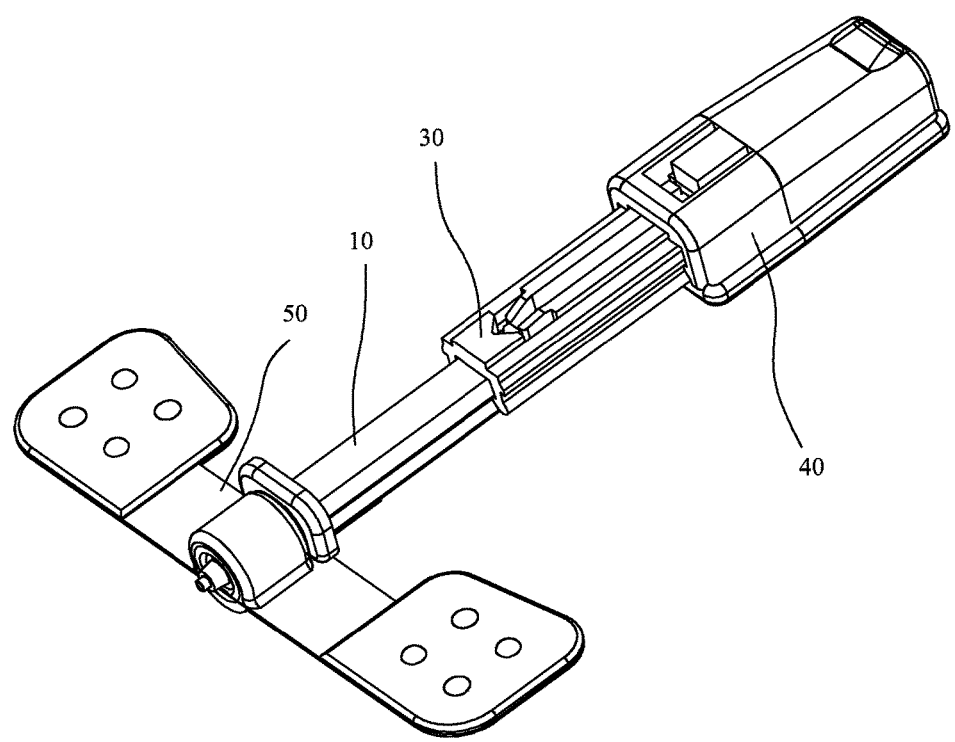
FIG. 9 is a schematic structure view of a preferred embodiment of the present invention when the operating handle is sleeved with the needle base.
Figure 10:
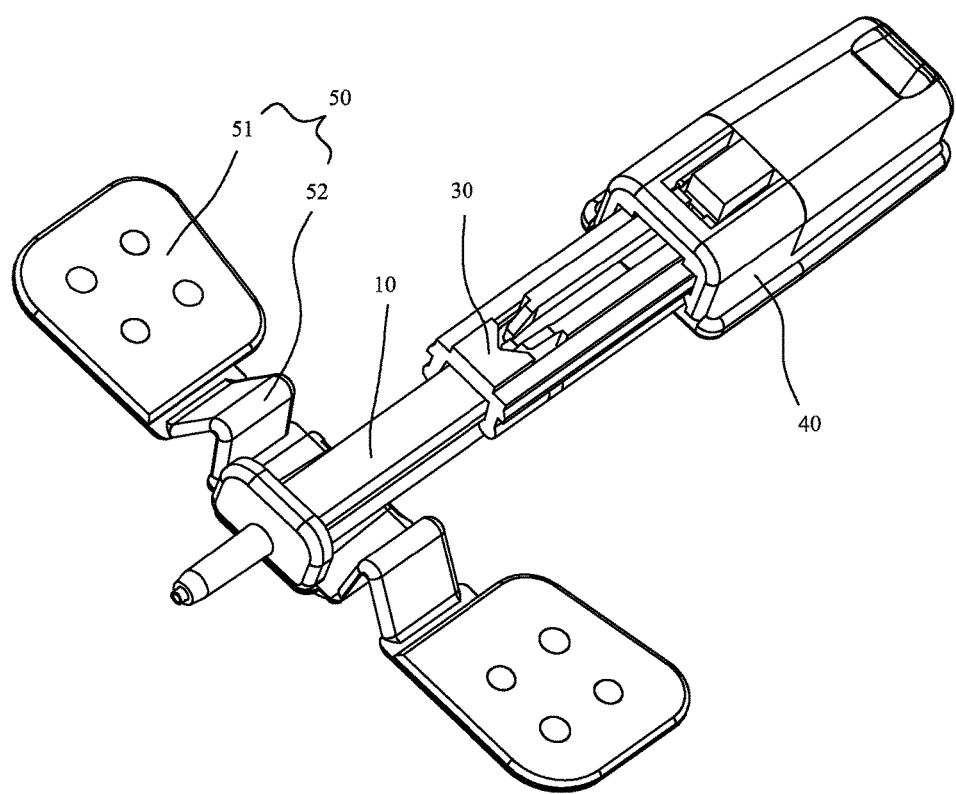
FIG. 10 is a schematic structure view of a preferred embodiment of the present invention when the operating handle has bent portion.

In order to use more conveniently, an operating handle 50 is arranged at rear end of the needle base, the operating handle 50 is provided with at least one wing portion 51. There may be one wing portion 51, which is located at one side of the needle base 10. There also may be two wing portions 51, and two wing portions 51 are located at both sides of the needle base 10 separately. There may be a variety of methods to connect the operating handle 50 and the needle base 10, and the operating handle 50 can also be integrally formed with the needle base 10; or as shown in FIG. 6, the operating handle 50 is clamped by the needle base 10; or as shown in FIG. 9, the operating handle 50 is sleeved with the needle base 10. As shown in FIG. 10, the operating handle 50 can further comprise a bent portion 52, and the bent portion 52 is arranged between the wing portion 51 and the needle base 10. The operating handle which can be bent is easy to operate.

After use of the needle device, pressing the second sleeve part, pulling the needle base backward, making the needle head leave skin of human body. During the process of backward movement of the needle base, the first sleeve part slides backward with the needle base, and the second sleeve part remains still. When the protrusion portion is restricted by the elastic limit portion inside the through hole, the first sleeve part clamps the needle base; when the second blocking portion blocks the third blocking portion, the first sleeve part will not slide backward, and the first blocking portion blocks the elastic button, to prevent the first sleeve part sliding forward. While the first sleeve part and the second sleeve part will cover the needle head on the needle base. The first sleeve part and the second sleeve part will not rebound, which cover the needle head and prevent the needle hurting people or objects. The cushion is a flat surface, which directly contacts with skin of human body, so that the skin of human body will not be uncomfortable in the process of operation, thereby improving comfort level during using process.

The needle device of the present invention has advantages that the operator operates conveniently when using, and the skin of patients is comfortable, the needle head can be covered quickly by the sleeve part on the needle base after use, and the connection between the sleeve part and needle base is tight, the sleeve part will not rebound, security of products is improved effectively.

In the description of the present invention, it needs to be understand that the directions or position relationships indicated by the term "upper", "lower", "front", "rear", "left", "right", "vertical", "horizontal", "top", "bottom", "inside", "outside" and so on are based on the directions or position relationships shown in the drawings, only in order to facilitate the description of the present invention and the simplified description, rather than indicate or suggest that the described device or unit must have a specific direction, or must be configured or operated in particular direction, accordingly, it can't be understand as restrictions on the present invention.

Although the specific embodiments of the present invention are illustrated as above, those skilled in the art will appreciate they are exemplary and the protection scope of the present invention is defined by the claims attached. Those skilled in the art can modify or amend these embodiments without deviating the scope and spirit of the present invention, but all of these modifies and amends are within the protection scope of the present invention.

What is claimed is:

1. A needle device, comprising a needle base and a needle head being placed in the needle base, wherein a first sleeve part slides on the needle base, a second sleeve part slides on the first sleeve part; at least one protrusion portion is arranged on an upper surface of the needle base, a through hole is arranged at a rear end of the first sleeve part, at least one elastic limit portion is arranged in the through hole, the elastic limit portion prevents the protrusion portion from moving toward a fixed end of the elastic limit portion when the protrusion portion moves to a position between an inner wall of the through hole and a free end of the elastic limit portion; a limit apparatus is arranged between the first sleeve part and the second sleeve part; wherein the limit apparatus comprises a first blocking portion, a second blocking portion, a third blocking portion and an elastic button; the first blocking portion and the second blocking portion are arranged on an upper surface of the first sleeve part, the elastic button is arranged on an upper surface of the second sleeve part, the third blocking portion is arranged on a lower surface of the second sleeve part, the second blocking portion prevents the third blocking portion from further moving when the elastic button moves to a position in front of the first blocking portion.

2. The needle device of claim 1, wherein the first sleeve part further has a bar groove, the bar groove is communicated with the through hole, the bar groove is located above the protrusion portion.

3. The needle device of claim 2, wherein the needle device comprises two elastic limit portions, wherein the two elastic limit portions are separately located at both sides of the bar groove.

4. The needle device of claim 3, wherein the distance between the free ends of two elastic limit portions is less than the distance between the fixed ends of two elastic limit portions.

5. The needle device of claim 2, wherein the needle device comprises two elastic limit portions, wherein the two elastic limit portions are both located at one side of the bar groove; the needle device comprises two protrusion portions, and the two protrusion portions match with two elastic limit portions respectively.

6. The needle device of claim 2, wherein the needle device comprises four elastic limit portions, wherein the two elastic limit portions are located at one side of the bar groove, and the other two elastic limit portions are located at the other side of the bar groove.

7. The needle device of claim 1, wherein a cushion is arranged at a bottom of the second sleeve part, wherein a bottom of the cushion is a flat surface, and the needle base and the first sleeve part are arranged inside a space surrounded by the cushion and the second sleeve part.

8. The needle device of claim 7, wherein a clamping portion is arranged at a lower section of the second sleeve part, and the cushion is clamped by the clamping portion.

9. The needle device of claim 7, wherein the cushion and the second sleeve part are integrally formed.

10. The needle device of claim 7, wherein a vertical distance between the needle head and the bottom of the cushion is larger than 0.05 mm.

11. The needle device of claim 1, wherein a length of the needle base is larger than 2 mm, a length of the first sleeve part is larger than 2 mm, and a length of the second sleeve part is larger than 2 mm.

12. The needle device of claim 1, wherein each of both sides of the needle base has a first slide railway, the first sleeve part has a first slide track matching with the first slide railway; each of both sides of the first sleeve part has a second slide railway, the second sleeve part has a second slide track matching with the second slide railway.

13. The needle device of claim 1, wherein a pressing portion is arranged on the upper surface of the second sleeve part.

14. The needle device of claim 1, wherein an operating handle is arranged at a rear end of the needle base, wherein the operating handle is provided with at least one wing portion.

15. The needle device of claim 14, wherein the needle device comprises one wing portion, the wing portion is located at one side of the needle base.

16. The needle device of claim 14, wherein the needle device comprises two wing portions, the wing portions are located at both sides of the needle base separately.

17. The needle device of claim 14, wherein the operating handle is sleeved with the needle base, or the operating handle is integrally formed with the needle base, or the operating handle is clamped by the needle base.

18. The needle device of claim 14, wherein the operating handle further comprises a bent portion, the bent portion is arranged between the at least one wing portion and the needle base.

19. The needle device of claim 1, wherein both of the first sleeve part and the second sleeve part are slot shaped.

20. A needle device, comprising a needle base and a needle head being placed in the needle base, wherein a first sleeve part slides on the needle base, a second sleeve part slides on the first sleeve part: at least one protrusion portion is arranged on an upper surface of the needle base, a through hole is arranged at a rear end of the first sleeve part, at least one elastic limit portion is arranged in the through hole, the elastic limit portion prevents the protrusion portion from moving toward fixed end of the elastic limit portion when the protrusion portion moves to a position between an inner wall of the through hole and a free end of the elastic limit portion: a limit apparatus is arranged between the first sleeve part and the second sleeve part, wherein the limit apparatus comprises a first blocking portion, a second blocking portion, a third blocking portion and an elastic button: the first blocking portion and the second blocking portion are arranged on an upper surface of the first sleeve part, the elastic button is arranged on an upper surface of the second sleeve part, the third blocking portion is arranged on a lower surface of the second sleeve part, the second blocking portion prevents the third blocking portion from further moving when the elastic button moves to a position in front of the first blocking portion, wherein the first blocking portion comprises two strip portions, the strip portions are arranged on the upper surface of the first sleeve part, wherein the two strip portions are arranged to be parallel to each other, and the strip portions act as a sliding track of the third blocking portion.

* * * * *